(12) United States Patent
Lee

(10) Patent No.: US 11,541,413 B2
(45) Date of Patent: Jan. 3, 2023

(54) PORTABLE DIFFUSER

(71) Applicant: BLOOMY LOTUS LIMITED, Hong kong (CN)

(72) Inventor: Leander Lee, New York, NY (US)

(73) Assignee: BLOOMY LOTUS LIMITED, Central (HK)

( * ) Notice: Subject to any disclaimer, the term of this patent is extended or adjusted under 35 U.S.C. 154(b) by 0 days.

(21) Appl. No.: 17/223,258

(22) Filed: Apr. 6, 2021

(65) Prior Publication Data
US 2022/0314264 A1    Oct. 6, 2022

(51) Int. Cl.
*B05B 17/06*    (2006.01)
*B05B 17/00*    (2006.01)

(52) U.S. Cl.
CPC ...... *B05B 17/0676* (2013.01); *B05B 17/0638* (2013.01)

(58) Field of Classification Search
CPC ................. B05B 17/0676; B05B 17/0638
See application file for complete search history.

(56) References Cited

U.S. PATENT DOCUMENTS

| 4,258,885 A | * | 3/1981 | Legeza | ............ B05B 1/042 |
| | | | | 239/599 |
| 2006/0255548 A1 | * | 11/2006 | Halling | ............ F16J 15/0887 |
| | | | | 277/644 |
| 2014/0166776 A1 | * | 6/2014 | Fang | ............ A61M 15/0065 |
| | | | | 239/102.2 |
| 2019/0298980 A1 | * | 10/2019 | Besen | ............ A45D 34/00 |

* cited by examiner

*Primary Examiner* — Qingzhang Zhou
(74) *Attorney, Agent, or Firm* — Hamre, Schumann, Mueller & Larson, P.C.

(57) ABSTRACT

A fluid diffuser for atomization of essential oils can have a flexible seal used to reduce internal pressure of an air chamber adjacent to the atomizer. It can also use a cover and a sensor to control the operation of the atomizer based on the position of the cover. An atomizer housing portion of the diffuser can be removable and replaceable relative to a lower portion of the housing.

5 Claims, 7 Drawing Sheets

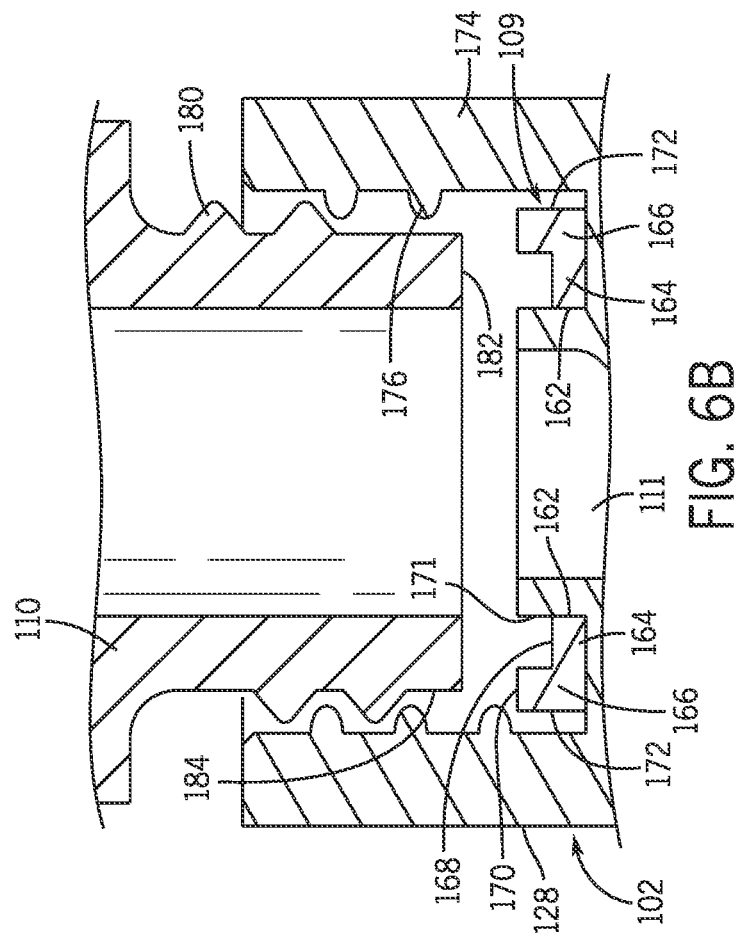
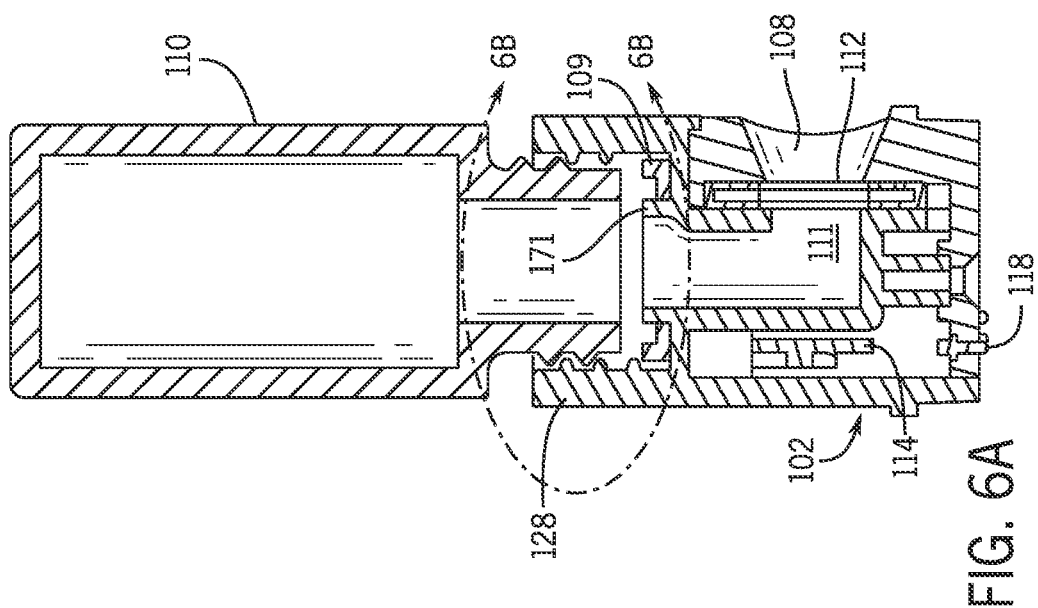

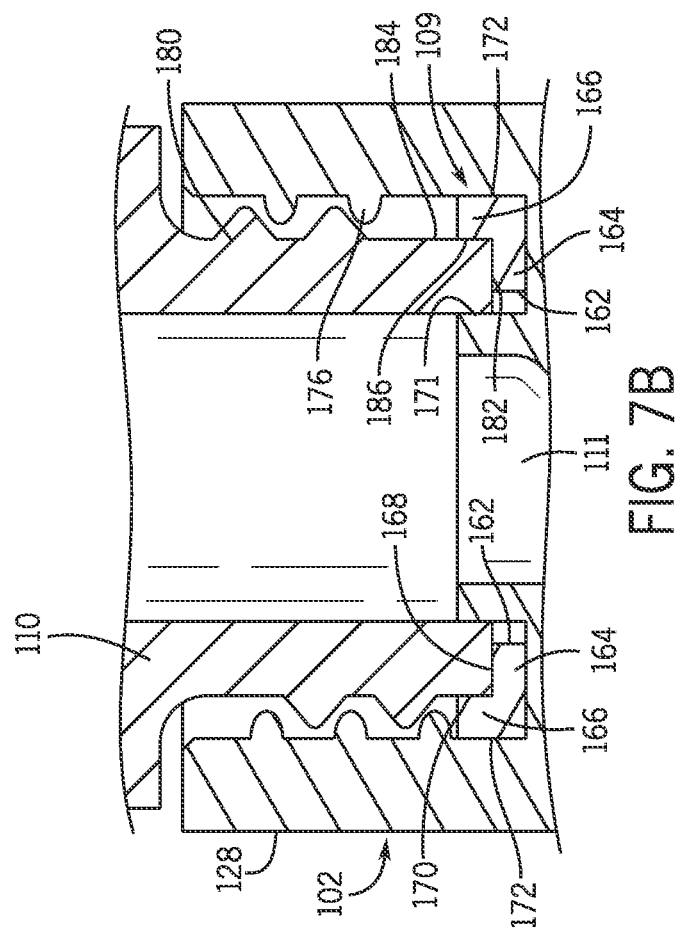
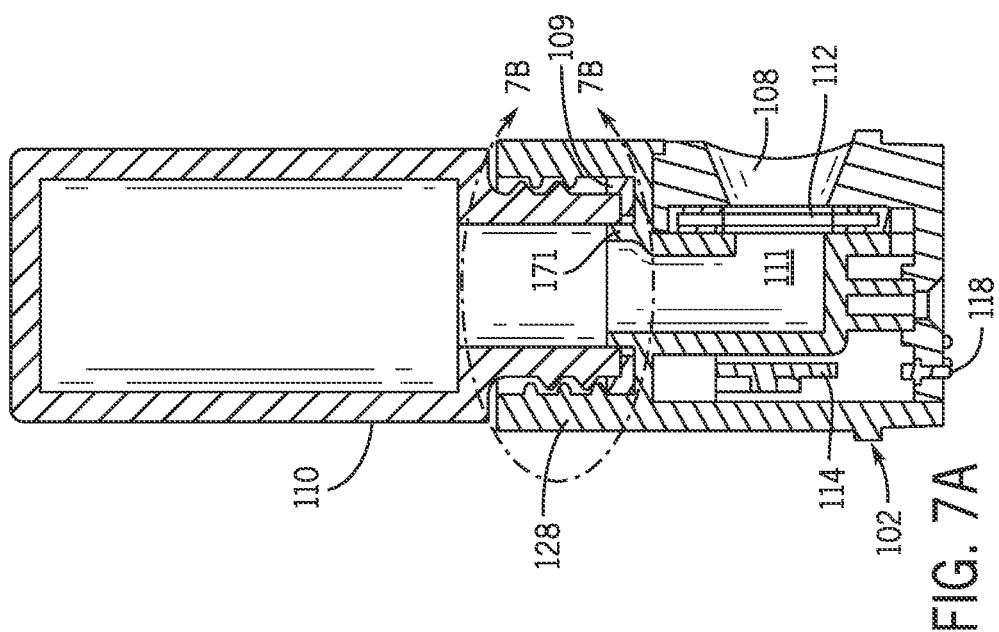

PORTABLE DIFFUSER

TECHNICAL FIELD

The present disclosure generally relates to portable diffuser devices for essential oils and other fluids and specifically relates to control systems, covers, modular components, and systems for reducing leakage from essential oil diffusers.

BACKGROUND

Fluid atomizers and diffusers are used to provide comfort, disinfect, and promote healing worldwide. Usually, users fill a reservoir or bottle with an essential oil or similar fluid of their choice, and the diffuser excites and disperses the fluid so that it is capable of being scattered in tiny droplets or clouds of vapor in the air around the diffuser. The vapor clouds or droplets are then breathed in or permitted to disperse across a surface by the user. These devices are commonly used as stationary devices, wherein the diffuser and the associated reservoir of fluid are substantially still as they operate.

Portable diffuser devices have gained popularity in recent years for users who want to enjoy the benefits of these devices in locations where there may be limited or temporary access to electricity, such as while traveling, hiking, camping, in a restaurant, or while using public transit. However, portable diffusers need to be compact, quiet, and lightweight and need to resist leaking. Frequently, portable diffusers fail to meet these needs or have low durability or quality. There is a constant need for improvements in the field of portable diffusers.

SUMMARY

One aspect of the present disclosure relates to a fluid diffuser comprising a housing defining a flow path from a first opening in the housing to a second opening in the housing, with the housing having a coupling portion adjacent to the first opening and configured to attach to a bottle, a porous electric atomizer positioned in the flow path, and a flexible seal positioned adjacent to the coupling portion and configured to expand in response to engagement with an end of the bottle.

In some embodiments, the fluid diffuser has a longitudinal axis extending centrally through the coupling portion, and the flexible seal comprises a first portion extending radially from the longitudinal axis and a second portion extending parallel to the longitudinal axis. The flexible seal can comprise a central opening aligned with the coupling portion. The flexible seal can be configured to engage a first surface of the bottle and a second surface of the bottle with the first and second surfaces being positioned at an angle relative to each other and with the angle being in a range extending from about 45-degrees to about 135-degrees. In one example, the surfaces can be positioned at an about 90-degree angle relative to each other. The flexible seal can be configured to expand from a first position in which the flexible seal contacts a central shaft of the housing to a second position in which the flexible seal does not contact the central shaft. The coupling portion can comprise housing threads to engage bottle threads of the bottle, wherein engagement of the housing threads with bottle threads drives the bottle into the flexible seal. Expansion of the flexible seal can be configured to reduce air pressure in the flow path.

Another aspect of the disclosure relates to an atomizer device comprising a housing having a mount portion connectable to an end of a fluid bottle, an atomizer to atomize fluid passing into the housing from the fluid bottle through the mount portion of the housing, wherein attachment of the fluid bottle to the housing forms an air chamber from the fluid bottle to the atomizer, and a bottle seal configured to be positioned between the mount portion and the end of the fluid bottle, wherein the bottle seal reduces air pressure in the air chamber in response to connection of the fluid bottle to the mount portion of the housing.

In some embodiments, the bottle seal comprises an elastically resilient material. The bottle seal can radially expand to reduce air pressure in the air chamber. The bottle seal can comprise an inner radius less than an outer radius of the end of the fluid bottle, and wherein the inner radius expands to engage the outer radius when the bottle seal reduces air pressure in the air chamber. The bottle seal can be positioned at an end wall of the mount portion of the housing. The bottle seal can also be configured to change shape to reduce the air pressure as the fluid bottle is tightened to the mount portion. The bottle seal can be shaped substantially circular.

In yet another aspect of the disclosure, a diffuser for essential oils is provided which comprises an atomizer housing including an inlet opening, an outlet opening, a channel defined through the atomizer housing and connecting the inlet opening and the outlet opening, a microporous atomizer positioned in channel, and a first electrical connector having a first electrical contact. The diffuser can also include a second housing including a power source and a second electrical connector in electrical communication with the power source and having a second electrical contact. The atomizer housing can be reversibly mountable to the second housing with the first electrical connector in electrical communication with the second electrical connector and the first electrical contact abutting the second electrical contact.

In some embodiments, the atomizer housing is rotatably mountable to the second housing. The atomizer housing can comprise a seal positionable between a fluid reservoir attached to the atomizer housing to provide fluid to the channel. At least one of the first and second electrical contacts comprise a biased conductive protrusion.

In some embodiments, a cover is included that is movable between a first position covering the outlet opening and a second position exposing the outlet opening, wherein a position sensor is configured to enable provision of power from the power source to the microporous atomizer when the cover is in the second position. A magnetic sensor can be used to enable and disable the microporous atomizer in response to movement of a magnetic element in a cover for the atomizer housing or for the second housing.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

FIG. 6A is a side section view of the atomization housing with the bottle partially inserted.

FIG. 6B is a detail view of FIG. 6A.

FIG. 7A is a side section view of the atomization housing with the bottle fully inserted.

FIG. 7B is a detail view of FIG. 7A.

Figure 1:
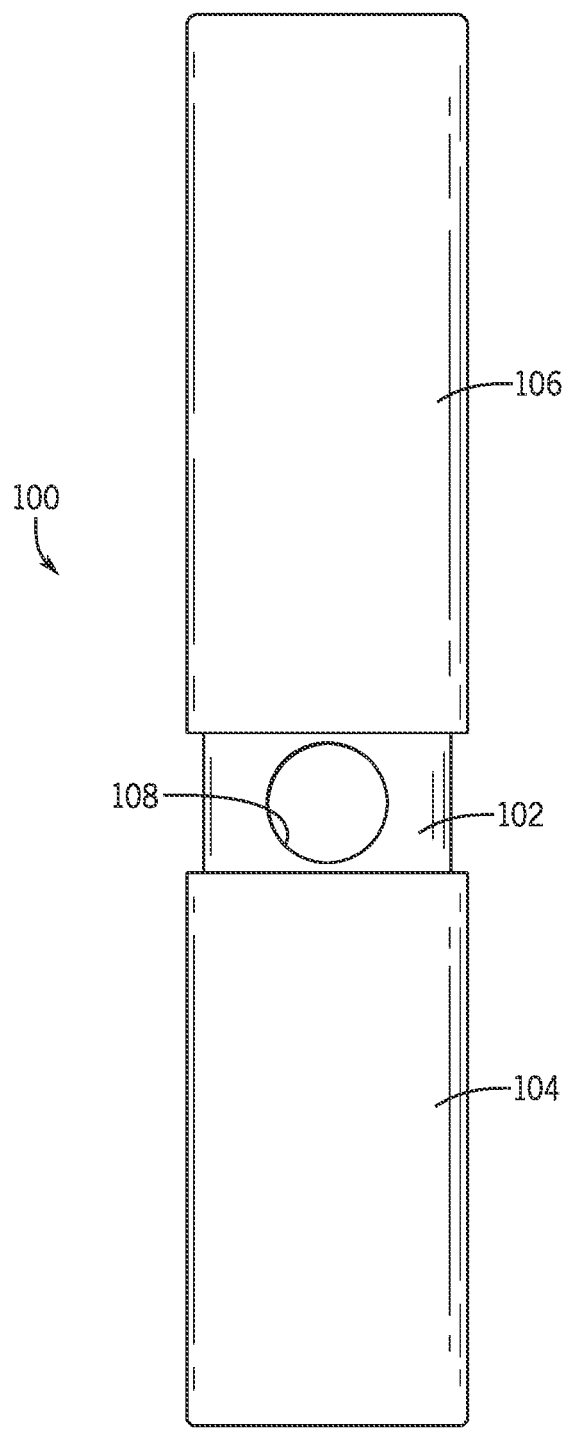
FIG. 1 is a front side view of a diffuser.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Portable diffusers for fluids such as essential oils are often inconvenient to use and difficult or impossible to repair. A portable diffuser may use an ultrasonic porous electric atomizer to diffuse oil or a mixture of oil and another fluid (e.g., water). A user can attach a bottle of the fluid to an atomizer housing of the diffuser by a threaded connection that places the opening of the bottle in fluid communication with a passage through the housing. Once the housing is properly oriented, the fluid can then advance through the passage in the housing until it comes into contact with the atomizer. The atomizer excites the fluid, and the fluid then passes through the atomizer and emerges from the diffuser as a mist or cloud of vapor and tiny droplets.

In some cases, attachment of the bottle to the diffuser housing can increase the air pressure within the fluid chamber of the bottle and the housing passage connecting the bottle to the atomizer. The pressure increase is due to the sealed volume of the bottle and passage reducing slightly when the bottle is sealed to the housing of the diffuser. The increased air pressure in the bottle and passage can cause the fluid to seep through the pores of the atomizer. As a result, the atomizer leaks, leading to unwanted loss of fluid and potential damage to nearby objects (e.g., leakage into a purse, wallet, backpack, etc.). Additionally, the fluid that seeps through the atomizer forms large droplets on its outer surface that block the pores and make the atomizer unable to atomize the fluid through those pores.

Embodiments of the present disclosure relate to diffusers configured to prevent this type of positive-pressure-induced atomizer leakage. In some embodiments, the diffuser includes a flexible seal that engages a mouth or outlet portion of the bottle and prevents leakage between the bottle and the housing of the diffuser. The seal is also configured to reduce the pressure in the bottle and passage, thereby reducing or eliminating leakage through the pores of the atomizer. To do so, the seal is configured to deform when engaging the bottle, and the deformation of the seal causes the volume of fluid or air in the bottle to expand in a manner that reduces air pressure in the bottle. The small change in internal pressure of the bottle and passage is sufficient to counter the small increase in internal pressure caused by the attachment of the bottle to the diffuser, so the fluid is not under a pressure differential when the air within the bottle and passage is compared to the air external to the diffuser.

The seal can deform in response to an outer diameter of the end of the bottle contacting an inner diameter of the seal, wherein the inner diameter of the seal is slightly smaller than the outer diameter of the bottle. Thus, when the bottle advances into the seal, the seal resiliently radially expands so that the inner diameter of the seal can fit around the outer diameter of the bottle. This expansion of the seal creates a small void where the seal was positioned before expanding (e.g., at the center of the seal), and the void increases the internal volume of the bottle and passage. The increased volume is filled by air or fluid from the bottle, thereby reducing internal pressure. In other words, the total sealed internal volume (i.e., the internal volume of the passage plus the internal volume of the bottle) slightly increases as the seal is deformed due to the seal increasing the available space in the internal volume for air or fluid to occupy.

Another aspect of the disclosure relates to improving the portability, ergonomics, and durability of a portable diffuser. In some embodiments, the diffuser comprises a cover used to contain and protect the bottle of fluid and the atomizer housing. The cover can be movable between a covering position (that blocks an opening on the atomizer housing and that prevents contaminants and debris from entering the outlet of the housing) and an uncovered or open position (that leaves the opening clear for the passage of fluid vapor and droplets to exit the diffuser). The cover can also be used to control operation of the diffuser. For instance, the cover can comprise a ferromagnetic element that is detectable by a sensor (e.g., a Hall effect sensor) in the atomizer housing. The positioning of the cover can therefore be sensed, such as whether it is in a covering position or in an uncovered position relative to the outlet opening of the diffuser. A controller or control logic board can be used to control the operation of the atomizer in response to a signal or reading from the sensor, whereby the atomizer can be activated and operated while the exit opening of the diffuser is uncovered. The atomizer can be deactivated while the exit opening is covered by the cover. In this manner, the number of parts of the diffuser is reduced (as compared to a diffuser that uses switches or buttons to control operation), and the diffuser is prevented from expelling vapor or droplets while the outlet opening is covered (thereby limiting fluid spoilage and waste).

Additionally, some portable diffusers are prone to failures related to defective atomization devices. When an atomizer fails in a conventional diffuser, the diffuser needs to be replaced due to the atomizer being non-removable and non-repairable. Thus, another aspect of the present disclosure relates to a portable diffuser having an atomizer housing that is separable and removable from the rest of the diffuser. The atomizer housing can be a component part that is removable and replaceable from the second, lower housing and cover if the atomizer within the atomizer housing fails to function properly. To enable detachment and replacement of the atomizer housing, the diffuser can include a set of reversibly user-separable electrical connections between the atomizer housing and a second housing containing a power source (e.g., battery) and other components needed to operate the diffuser (e.g., a controller). The atomizer housing can have electrical connectors that can be disconnected from electrical connectors of the second housing so that a new atomizer housing, with its own new electrical connectors, can be installed in its place.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

FIG. 1 is a front view of a portable diffuser 100. The diffuser 100 can include an atomizer housing 102 connected to a second, lower housing 104 and at least partially covered by a cover 106. In the view of FIG. 1, the atomizer housing 102 has its outlet opening 108 exposed due to the cover 106 being moved longitudinally away from the lower housing 104 (i.e., upward).

Figure 2:
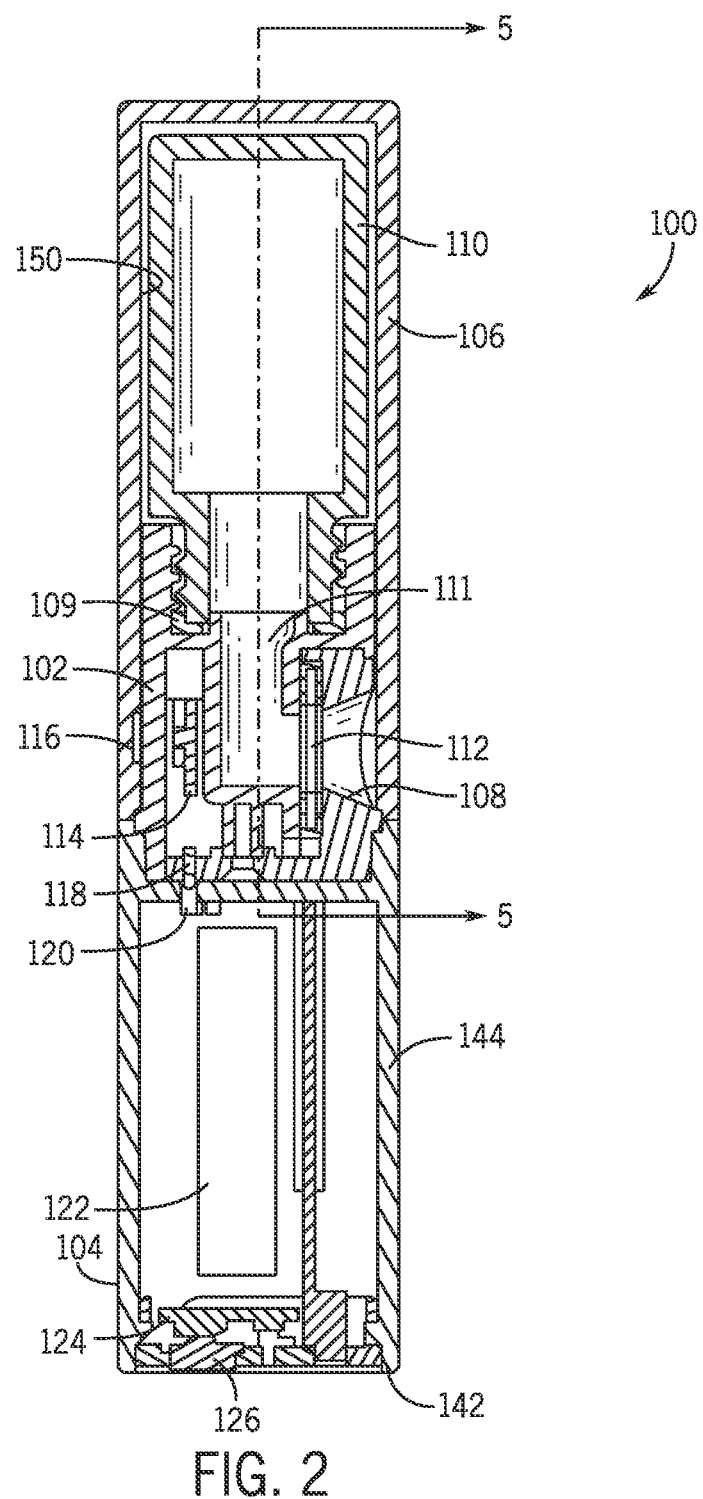
FIG. 2 is a side section view of the diffuser of FIG. 1.

FIG. 2 shows a right side section view through the diffuser 100 with the cover 106 in a position relative to the atomizer housing 102 that encloses the outlet opening 108. A fluid reservoir or bottle 110 is positioned inside the cover 106 and attached to the atomizer housing 102. See also FIG. 3. A seal 109 is positioned between the bottle 110 and the atomizer housing 102. The atomizer housing 102 contains a passage 111 or internal tube that defines a fluid flow path and air chamber linking the bottle 110 to an atomizer 112 that separates the passage 111 from the outlet opening 108. The atomizer housing 102 also contains a sensor 114 within its outer walls that is positioned on the opposite side of the atomizer housing 102 from the outlet opening 108. The cover 106 can include a ferromagnetic material 116 configured to be positioned adjacent to the outside of the surface of the atomizer housing 102 within which the sensor 114 is positioned. The sensor 114 can thereby detect the position of the cover 106 relative to the atomizer housing 102 by detecting the presence or absence of the ferromagnetic material 116 of the cover 106.

The atomizer housing 102 can also include a set of electrical connectors 118 configured to establish electrical connections between a bottom end of the atomizer housing 102 and a second set of electrical connectors 120 at a top end of the lower housing 104. The second set of electrical connectors 120 provides an electrical connection to electrical components in the lower housing 104, such as, for example, to a power source 122 (or other power source connection), a control board 124, and input devices (e.g., button 126). Thus, electrical connectors 118, 120 can provide electrical communication between components in the atomizer housing 102 and the lower housing 104 so that the atomizer 112 and sensor 114 can function as if they were directly connected to electrical components in the lower housing 104.

Figure 3:
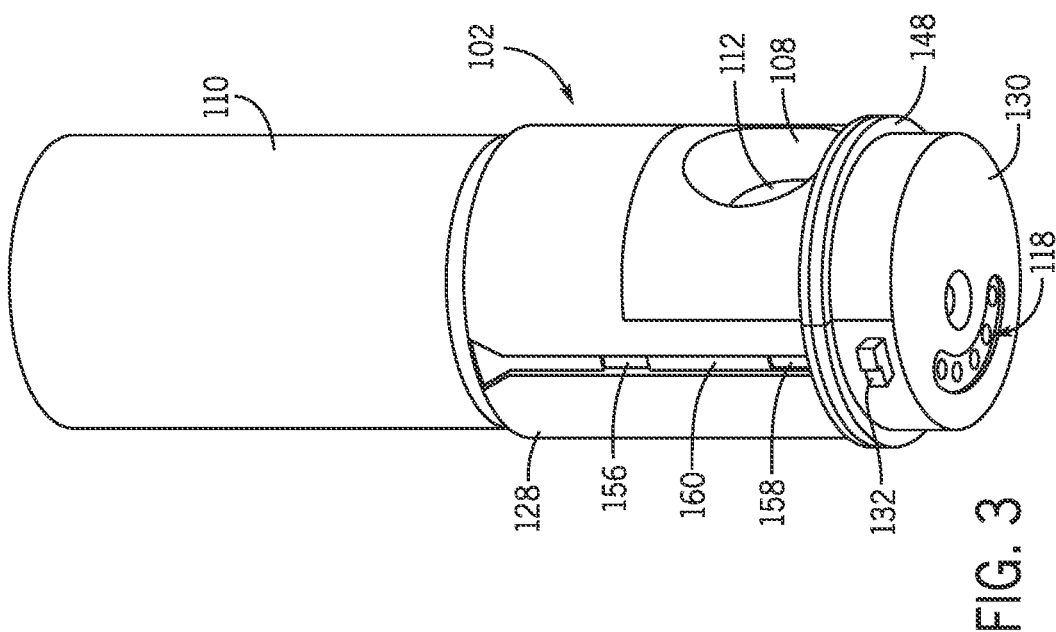
FIG. 3 is an orthographic view of an atomizer housing and bottle of the diffuser.

The atomizer housing 102 is shown separate from the lower housing 104 and uncovered 106 in the orthographic view of FIG. 3. The atomizer housing 102 includes an upper end 128 (i.e., a bottle-coupling portion or mount portion) and the lower end 130. The outlet opening 108 is positioned between the upper and lower ends 128, 130, and the set of electrical connectors 118 is positioned at the lower end 130. The bottle 110 is attached at the upper end 128 by engaging threads around the mouth end of the bottle 110 to internal threads of the upper end 128, as shown and described in more detail in connection with FIGS. 6A-7B below.

Figure 4:
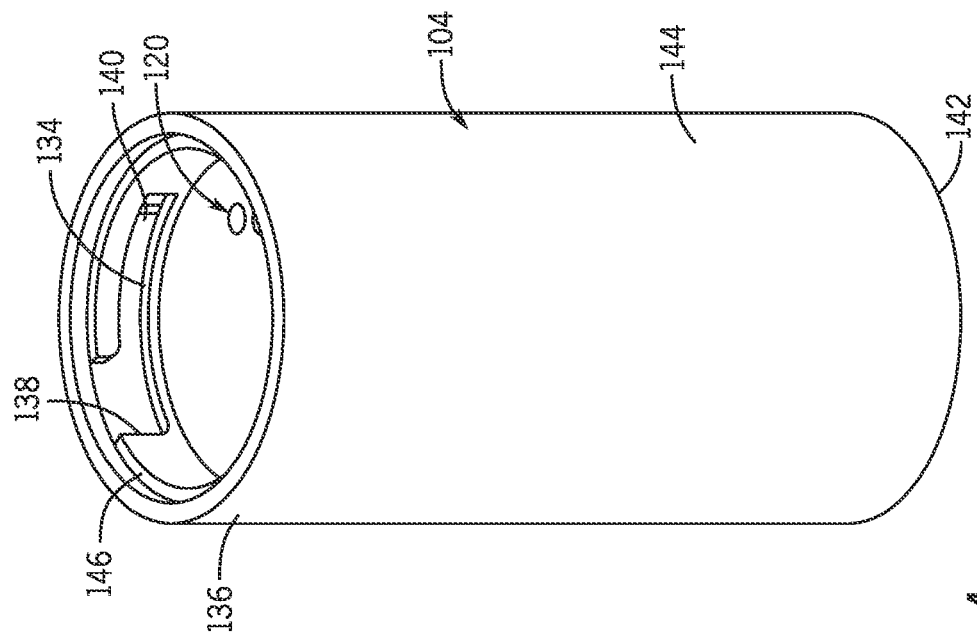
FIG. 4 is an orthographic view of a lower housing of the diffuser.

The atomizer housing 102 also includes at least one protrusion 132 configured to be received by and held within a recess 134 in the lower housing 104 at its upper end 136 (see FIG. 4). Thus, the atomizer housing 102 is attachable to the lower housing 104 by inserting the protrusion 132 into a mouth section 138 of the recess 134 and rotating the atomizer housing 102 relative to the lower housing 104 to move the protrusion 132 into the end section 140 of the recess 134. In that position, the protrusion 132 is prevented from being pulled vertically upward and out of the recess 134 unless the protrusion 132 is rotated back to the mouth section 138. Thus, the atomizer housing 102 and lower housing 104 can thereby be temporarily attached to each other by interference of parts between the protrusion 132 and recess 134. The housings 102, 104 can therefore be rotatably mountable to each other. If necessary, they can be disconnected from each other for simple and convenient user replacement of one or the other. This can be especially beneficial if the atomizer 112 malfunctions, leaks, becomes clogged, or similarly fails. Additionally, as illustrated by FIGS. 2, 3, and 4, rotation of the atomizer housing 102 relative to the lower housing 104 can bring the first set of electrical connectors 118 into alignment and engagement with the second set of electrical connectors 120. In some embodiments, the housings 102, 104 can be attached to each other by engaging threads, by interlocking parts, by adhesive or welding, etc.

The outlet opening 108 on the atomizer housing 102 can be oriented radially outward relative to the vertical longitudinal axis of the diffuser 100 and in a direction perpendicular to the longitudinal axis that extends centrally through the opening of the bottle 110 and the opening on the atomizer housing 102 to which the bottle 110 is connected. In some embodiments, multiple outlet openings can be used. The outlet opening 108 can have a conical shape in the atomizer housing 102 that helps facilitate expansion and spreading of the vapor and droplets emitted through the atomizer 112.

The lower housing 104, as shown in the orthographic view of FIG. 4, can have a substantially flat bottom surface 142 and can be used to provide a stand for the atomizer housing 102 so that the diffuser 100 can sit on a flat surface without falling over. The lower housing 104 can have an outer housing surface 144 that comprises the same material and appearance as the outer surface of the cover 106 and that has an equal diameter to the cover 106 so that the diffuser 100 has a smooth, uniform appearance when the cover 106 is in the closed or outlet-covering position. The upper end 136 of the lower housing 104 can also include an inner shelf 146 that is recessed relative to the extreme top end of the lower housing 104 and that acts as a rest surface for a housing ring 148 on the atomizer housing 102. See FIGS. 3-4. Thus, as shown in FIG. 2, the atomizer housing 102 can have its housing ring 148 rest on the inner shelf 146 to stabilize and help align the atomizer housing 102 with the lower housing 104 to improve their attachment stability and thereby ensuring consistent contact between the electrical connectors 118, 120.

Figure 5:
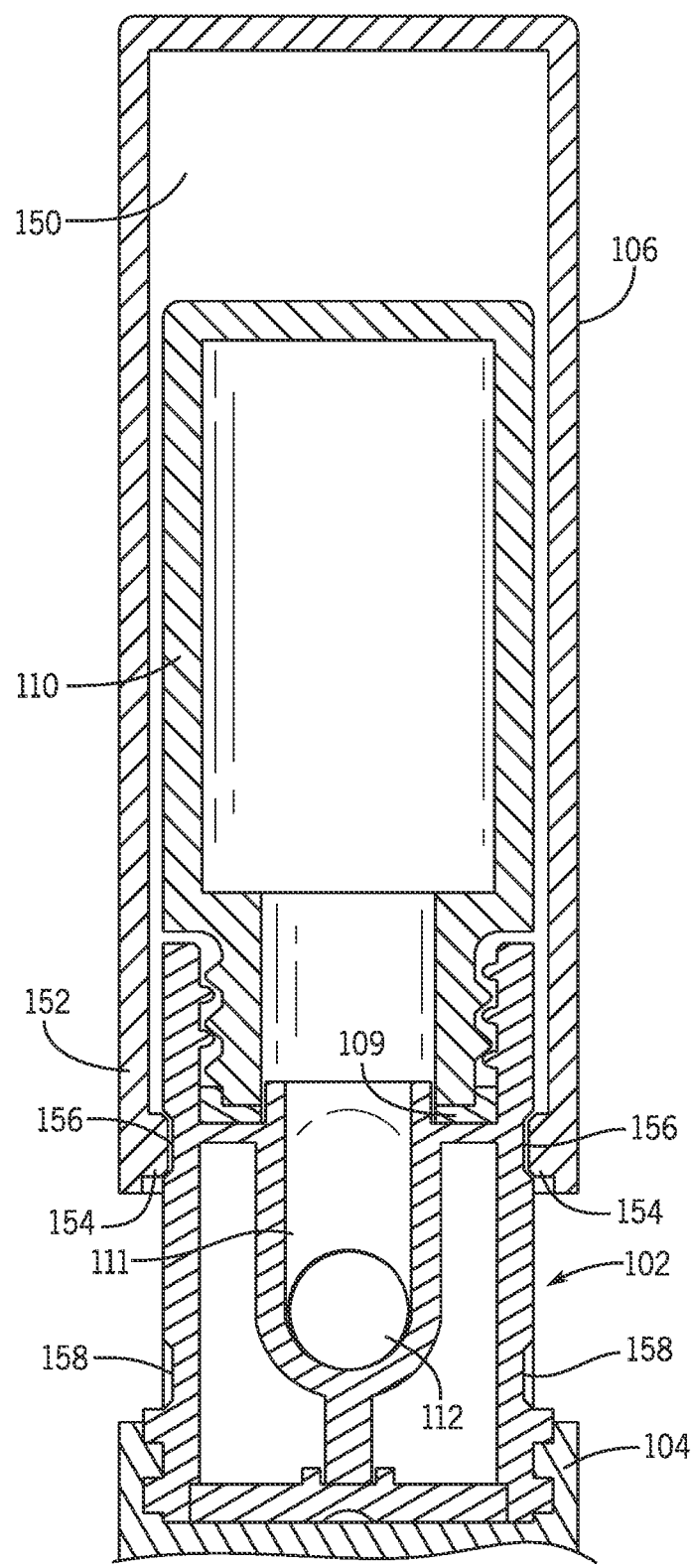
FIG. 5 is a section view of the diffuser as taken through section lines 5-5 in FIG. 2.

The cover 106 is a movable enclosure and shell that, in some embodiments, can be used to control the operation of the atomizer 112 and, potentially, other electronic components of the diffuser 100. The cover 106 can comprise a generally non-ferromagnetic material such as a plastic, wood, or composite material and can define an internal cavity 150 having sufficient inner diameter and depth to receive the bottle 110 and any portions of the atomizer housing 102 that protrude from the lower housing 104, as shown in FIG. 2. As shown in the section view of FIG. 5, which is taken through section lines 5-5 in FIG. 2, at least the bottom end 152 of the cover 106 can have one or more inward-directed protrusions 154. The protrusions 154 can be selectively moved between an upper position in which the protrusions 154 are within upper recesses 156 and a lowered position in which the protrusions 154 are in lower recesses 158 shown in FIGS. 3 and 5.

The upper and lower recesses 156, 158 can be formed in a side channel 160 of the atomizer housing 102 (see FIG. 3) to guide the protrusions 154 parallel to the longitudinal axis of the diffuser 100. As a result, the cover 106 and its protrusions 154 are slidable along the channel 160 between a first position shown in FIG. 2 and a second position shown in FIGS. 1 and 5, and in each of those positions, the cover 106 can be biased in place by the protrusions 154 fitting into the recesses 156, 158. Sliding the cover 106 with sufficient force to expand the bottom end 152 of the cover 106 and to slide the protrusions 154 out of the recesses 156, 158 can allow the cover to move relative to the atomizer housing 102 or to be removed from the atomizer housing 102 completely, for example, as shown in FIG. 3. Removal of the cover 106 can permit the user to access the bottle 110 to remove or adjust the bottle 110.

The ferromagnetic material 116 of the cover 106 can be positioned on the cover 106 in a location configured to move adjacent to the sensor 114 of the atomizer housing 102. The ferromagnetic material 116 can include a magnetic material configured to emit a magnetic field with sufficient strength to be detected by the sensor 114 when the ferromagnetic material 116 is next to the sensor 114, such as when the ferromagnetic material 116 and the sensor 114 are radially aligned in the position shown in FIG. 2. The magnetic strength of the ferromagnetic material 116 and the sensitivity of the sensor 114 can be selected and configured to enable the controller to which the sensor 114 is connected to distinguish between when the cover 106 is in the lowered or covering position of FIG. 2 relative to the sensor 114 and when the ferromagnetic material 116 is moved upward or otherwise more spaced away from the sensor 114.

Thus, the sensor 114 can be a position sensor for the cover 106 that detects whether the cover is obscuring the outlet opening 108 or not. The sensor 114 can also be a position sensor configured to detect whether the cover 106 is mounted to the atomizer housing 102 or lower housing 104 at all (or not). The signal produced by the sensor 114 as result of detecting or not detecting the cover 106 can be used to enable or disable operation of the atomizer 112 so that the atomizer 112 does not vaporize fluid while the cover 106 is covering the outlet opening 108 or while the cover 106 is completely removed and a user is trying to access the bottle 110 or provide maintenance to the atomizer housing 102. In some embodiments, other types of position-detecting systems can be used with the cover 106, such as, for example, an optical sensor in the atomizer housing 102 configured to detect the cover 106 or one or more buttons on the atomizer housing 102 or lower housing 104 that are pressed by the cover 106 depending on whether it is in a raised or lowered position.

The bottle 110 can be a conventional bottle used to hold fluids such as essential oils. The bottle 110 can be configured to have a standard size and shape that is compatible with makers of essential oils and those that use them. For instance, the bottle 110 can have an internal volume of about 5 mL to about 15 mL and can have a standard neck and mouth size, neck thread size and count, and other conventional characteristics. The bottle 110 can beneficially comprise a transparent or translucent material that allows a user to see how much fluid remains in the bottle 110 while it is being used and emptied into the atomizer housing 102. Thus, by removing the cover 106 or by looking through an optional window in the cover 106, the amount of fluid in the bottle 110 can be observed by a user.

The atomizer 112 can be a humidifier driver or mist generator configured to atomize fluid within the atomizer housing 102. The atomizer 112 can comprise a disk shape having multiple layers of material configured to move (e.g., vibrate). In an example embodiment, the atomizer 112 can be an ultrasonic atomizing piezoelectric transducer configured for humidifying air, aromatherapy, essential oil diffusion, nebulization, spreading disinfectant, and similar activities. The atomizer 112 can comprise a microporous metal sheet through which ultrafine particles of fluid can pass when excited by ultrasonic vibrations of the atomizer. Thus, the atomizer 112 can act as a fluid barrier in the passage 111 when it is not active, and the atomizer 112 can permit fluid to pass through itself when it is activated and the fluid is atomized. The atomizer 112 can be welded in place within the atomizer housing 102 such that it becomes an integral part of the atomizer housing 102. Thus, if the atomizer 112 fails or declines in function, it can be replaced by replacing the atomizer housing 102 without having to also replace the lower housing 104 or its internal components.

The first and second sets of electrical connectors 118, 120 can comprise metallic or other conductive materials configured to provide electrical communication when in contact with each other. In an example embodiment, at least one of the first or second sets of electrical connectors 118, 120 can include biased pins or protrusions that protrude from the housing 102 or 104 to engage the other sets of electrical connectors. For instance, as shown in FIG. 6A, the first set of electrical connectors 118 can extend downward from the bottom surface of the atomizer housing 102 due to an internal spring function of the electrical connectors 118 that biases the connectors outward (e.g., a set of coil springs, leaf springs, or other biasing members (not individually shown)). When the atomizer housing is fully mounted to the lower housing 104, the pins can be pushed inward when by contact with the second set of electrical connectors 120, and the spring function can help maintain a consistent and uninterrupted connection between the connectors 118, 120 until the atomizer housing 102 is rotated and removed from the lower housing 104.

The power source 122 can include an energy storage device such as a rechargeable battery usable to provide power to the atomizer 112. Thus, the electrical connectors 118, 120 can provide a power connection between the power source 122 and the atomizer 112. Additionally, wiring (not shown) can be used to connect the atomizer 112 to the first set of electrical connectors 118 and to provide electrical communication between the sensor 114 and the first set of electrical connectors 118. In some embodiments, the power source 122 can include a connection point for an external power source or a removable power source. For example, the power source 122 can comprise connections for alkaline batteries or similar disposable or separable batteries stored in the lower housing 104. Similarly, in another example, the power source 122 can comprise connections configured to engage with a power plug to provide power to the diffuser 100 from an electrical outlet. Thus, the power source 122 shown as a battery in FIG. 2 is merely representative of various types of power sources and connections to power sources that can be used by those having skill in the art and having the benefit of the present disclosure. Moreover, additional wiring (not shown) can provide electrical communication between the power source 122, the second set of electrical connections 120, and the control board 124 through a series of these components or other similar combinations of elements. This can help ensure that power is provided as needed to the atomizer 112 via the second set of electrical connections 120.

The control board 124 can comprise a substrate having control logic such as a printed circuit board (PCB). The control board 124 can receive a signal from the sensor 114 and can control the provision of power from the power source 122 to the atomizer 112 based on the state of the sensor 114, as described above. In some embodiments, the control board 124 can also receive control signals from an input device, such as a button 126, a dial, another sensor, or similar device that can control a feature not controlled by the output of the sensor 114. For example, the input device can be used to turn the sensor 114 on or off, can control the rate or temperature of atomization by the atomizer 112, or can switch the power source provided to the atomizer 112 between a battery and a different power source, such as a wire to an electrical outlet. In some embodiments, the sensor 114 and ferromagnetic component 116 can be omitted, and the button 126 or other input device can be used to control the atomizer 112.

Figure 8:
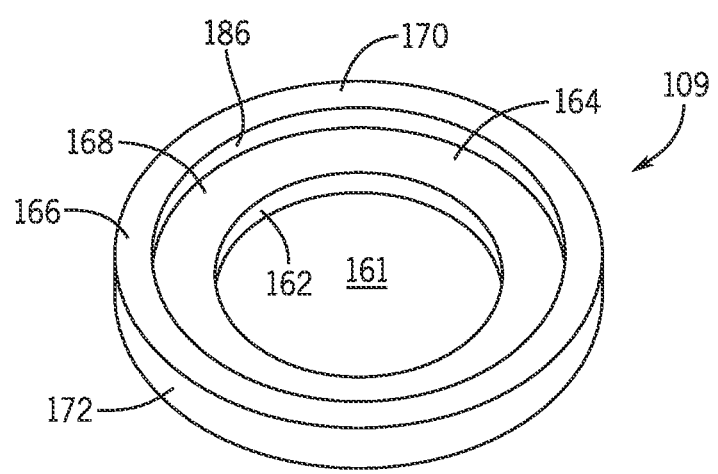
FIG. 8 is an orthographic view of a flexible seal of the diffuser.

FIGS. 6A-8 illustrate the features and operation of the seal 109 positioned between the bottle 110 and the atomization housing 102. FIGS. 6A and 6B show the bottle 110 in a condition partially inserted into the atomization housing 102, FIGS. 7A and 7B show the bottle 110 fully seated against the seal 109, and FIG. 8 shows an orthographic view of the seal 109 alone. As seen in FIG. 8, the seal 109 can include a central opening 161, a horizontal shelf portion 164 surrounding the central opening 161, and a vertical ring portion 166 surrounding the horizontal shelf portion 164. The horizontal shelf portion 164 can extend radially from the longitudinal axis of the seal 109 (which extends centrally through opening 161), and the vertical ring portion 166 can extends parallel to the longitudinal axis. The seal 109 can have a substantially annular shape so that fluid from the bottle 110 can pass through the central opening 161 and into the atomizer housing 102 at the upper end of the passage 111. Although the seal 109 is shown with a generally circular or o-shaped top profile, it will be understood by those having skill in the art that a variety of different seal or gasket-like shapes can be used, depending on the shape of the bottle 110 and the opening that the seal 109 needs to block and make fluid tight.

The horizontal shelf portion 164 can include a top surface 168, and the vertical ring portion 166 can include a top surface 170. The central opening 161 can have a cylindrical inner sidewall 162. When the seal 109 is at rest, as shown in FIG. 6B, the inner sidewall 162 can engage an outer surface of a central shaft or central tube 171. An outer sidewall 172 can be spaced away from and out of contact with an outer tube 174. The outer tube 174 is positioned radially outward relative to the outer sidewall 172 and the rest of the seal 109. The outer tube 174 can include an inner surface with a plurality of threads 176 configured to engage with threads 180 of the bottle 110, as shown in FIGS. 6A through 7B. Accordingly, as the bottle 110 is advanced into the outer tube 174 and the threads 176, 180 engage, the end face 182 of the bottle 110 can be positioned partially overlaying and above the top surfaces 168, 170 of the seal 109.

As the bottle 110 is further advanced, such as to the position shown in FIG. 7B, the end face 182 receives the central tube 171 of the atomizer housing 102 and comes into engagement with top surface 168 of the seal 109. In this position, the inside of the bottle 110 and passage 111 can be referred to as an air chamber. Between depositions shown in FIGS. 6B and 7B, the end face 182 comes into contact with top surface 170, and because the seal 109 is made of flexible material, such as rubber, thermoplastic polyurethane, and similar elastically resilient materials, the vertical ring portion 166 of the seal 109 deforms radially outward in contact with the end face 182 and expands so that the vertical ring portion 166 moves out towards the outer tube 174 and receives the bottle 110 with a side surface 184 of the bottle contacting the vertical ring portion 166 at an intermediate sidewall 186 (see FIG. 8), as shown in FIG. 7B. Thus, the bottle 110 can engage the seal 109 at a first surface (end face 182) and a second surface (side surface 184) that are positioned at an about 90-degree angle relative to each other. In other embodiments, these bottle surfaces can be positioned at other angles relative to each other, such as at an angle lying in a range extending between about 45 degrees and about 135 degrees, such as when the end face 182 has an outer or inner beveled edge. As shown in FIG. 6B, the inner radius of the intermediate sidewall 186 of the seal 109 can be less than the outer radius of the side surface 184 of the bottle 110, and as shown in FIG. 7B, that inner radius can expand to engage the outer radius when the bottle seal 109 reduces air pressure in the bottle 110 and passage 111.

Furthermore, as shown in FIG. 7B, the extension of the vertical ring portion 166 causes the inner sidewall 162 to move away from the central tube 171 of the atomizer housing 102, thereby creating a gap or void between the seal 109 and the central tube 171. When this gap or void appears, the vertical outer ring 166 has already or is immediately in sealing contact against the bottle 110. As a result, the gap or void fills with air that is sealed or trapped in the passage 111 and the internal volume of the bottle 110. In other words, air in the bottle 110 or passage 111 can be drawn between the inner surface of the bottle 110 and the central tube 171 by the vacuum created by the seal 109, and the volume of the air trapped in the bottle 110 and passage 111 increases, thereby reducing pressure in that volume.

The inclusion of this expandable seal 109 helps prevent leakage of fluid from the bottle 110 or passage 111 at the interface between the bottle 110 and the atomizer housing 102, and it also helps to reduce air pressure within the bottle 110 and passage 111. The small expansion of the seal 109 creates negative pressure on the air trapped in the bottle and passage, and that negative pressure is sufficient to reduce the internal air pressure of the passage 111 and bottle 110 to the level less than atmospheric pressure. For example, with air in the bottle 110 being at standard atmospheric air pressure of 101.325 kPa, the extension of the seal 109 can reduce the air pressure within the passage 111 to a range of about 101.300 kPa to about 101.325 kPa. In a particular embodiment, the seal 109 reduces pressure to about 101.310 kPa.

The slight reduction in internal pressure ensures that the air pressure inside the passage 111 does not exceed atmospheric pressure around the diffuser 100, which would cause positive pressure inside the passage 111 to drive fluid through the atomizer 112 even when the atomizer 112 is not active. However, with pressure inside the passage 111 matching or being less than the surrounding atmospheric pressure of the diffuser 100, such leakage is prevented or greatly reduced.

Without expansion of the seal 109, such as if a simple flat gasket were used in place of the seal 109, the attachment of the bottle 110 to the atomizer housing 102 would slightly compress the air in the volume of the bottle 110 and passage 111, thereby making the pressure in the passage 111 slightly exceed atmospheric pressure. In an example case, pressure within a 5 mL bottle would undesirably increase to 101.641 kPa. Accordingly, using the expandable seal 109 can save essential oil and other fluid in the passage 111, can keep the diffuser 100 clean or and more portable, and can extend the life of the diffuser 100 in general.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A fluid diffuser, comprising:
    a bottle;
    a housing defining a flow path from a first opening in the housing to a second opening in the housing, the housing having a coupling portion adjacent to the first opening and configured to attach to the bottle;
    a porous electric atomizer positioned in the flow path;
    an elastic seal positioned adjacent to the coupling portion and configured to expand in response to engagement with an end of the bottle;
    wherein the elastic seal is configured to expand from a first position in which the elastic seal contacts a central shaft of the housing to a second position in which the elastic seal does not contact the central shaft, to form a gap or void between the elastic seal and the coupling portion, and the gap or void fills with air that is sealed or trapped in the flow path and the internal volume of the bottle; and
    wherein expansion of the elastic seal is configured to reduce air pressure in the flow path.

2. The fluid diffuser of claim 1, wherein a longitudinal axis extends centrally through the coupling portion, and wherein the elastic seal comprises a first portion extending radially from the longitudinal axis and a second portion extending parallel to the longitudinal axis.

3. The fluid diffuser of claim 1, wherein the elastic seal comprises a central opening aligned with the coupling portion.

4. The fluid diffuser of claim 1, wherein the elastic seal is configured to engage a first surface of the bottle and a second surface of the bottle, the first and second surfaces being positioned at an angle relative to each other, the angle being in a range extending from 45-degrees to 135-degrees.

5. The fluid diffuser of claim 1, wherein the coupling portion comprises housing threads to engage bottle threads of the bottle, wherein engagement of the housing threads with bottle threads drives the bottle into the elastic seal.

* * * * *